United States Patent [19]

Mueller

[11] Patent Number: 5,143,851

[45] Date of Patent: Sep. 1, 1992

[54] METHOD FOR SEPARATING DIPHENYLUREA (DPU) AND PHENYLTHIOHYDANTOIN-TRYPTOPHAN (PTH-TRP) ALLOWING UNAMBIGUOUS IDENTIFICATION OF TRP IN AUTOMATIC SEQUENCE ANALYSIS

[75] Inventor: Thomas Mueller, Nyack, N.Y.

[73] Assignee: American Cyanamid Company, Stamford, Conn.

[21] Appl. No.: 493,062

[22] Filed: Mar. 13, 1990

[51] Int. Cl.[5] .................. G01N 33/00; B01D 15/08
[52] U.S. Cl. .................................. 436/89; 436/86; 436/87; 210/656; 210/198.2
[58] Field of Search ................. 436/89, 86, 87; 210/656, 198.2

[56] References Cited

U.S. PATENT DOCUMENTS 4,665,037  5/1987  Stolowitz ............................. 436/89

FOREIGN PATENT DOCUMENTS 8908835  9/1989  World Int. Prop. O. .

Primary Examiner—James C. Housel
Assistant Examiner—Thomas E. Daley
Attorney, Agent, or Firm—Alan M. Gordon; John C. Altmiller; Scott A. Brown

[57] ABSTRACT

A reverse-phase HPLC method is disclosed which allows the separation of DPU and PTH-Trp and, therefore, the correct assignment of tryptophan residues in an amino acid sequence. The method is based on a modification of the conventional HPLC gradient commonly used to elute and separate all PTH amino acids of interest in automated and manual sequencing. In one embodiment, using automated instruments manufactured by Applied Biosystems, gradient modification is achieved by changing the manufacturer-supplied gradient program which controls the operation of the HPLC pumps in the instrument. Using the methods of the present invention, the correct and reliable assignment of tryptophan residues is possible and was reproducible over time, even with small sample sizes.

2 Claims, 10 Drawing Sheets

FIG. 6

SAMPLE : A-11 LACTOGLOBULINE

Sample Amount: 100 pmol

| AAcid # | AAcid ID | R.Time (min) | C.Time (min) | Pmol (raw) | Pmol (-bkgd) | Pmol (+lag) | Pmol Ratio | AAcid ID |
|---|---|---|---|---|---|---|---|---|
| 1 | L | 24.92 | 24.88 | 26.14 | 26.32 | 27.76 | 103.53 | LEU |
| 2 | I | 24.12 | 24.05 | 31.21 | 30.61 | 31.92 | 133.80 | ILE |
| 3 | V | 19.75 | 19.73 | 22.08 | 21.58 | 23.89 | 139.49 | VAL |
| 4 | T | 7.87 | 7.98 | 20.32 | 19.78 | 22.93 | 58.14 | THR |
| 5 | Q | 7.30 | 7.43 | 17.79 | 17.26 | 20.38 | 86.82 | GLN |
| 6 | T | 7.85 | 7.98 | 15.85 | 15.45 | 17.99 | 45.61 | THR |
| 7 | M | 19.37 | 19.35 | 12.88 | 12.56 | 15.42 | 118.43 | MET |
| 8 | K | 24.55 | 24.48 | 12.46 | 11.76 | 14.41 | 72.25 | LYS |
| 9 | G | 8.32 | 8.37 | 15.77 | 13.62 | 17.39 | 58.60 | GLY |
| 10 | L | 24.95 | 24.88 | 15.43 | 13.50 | 17.58 | 65.54 | LEU |
| 11 | D | 5.20 | 5.28 | 14.79 | 13.71 | 17.65 | 123.94 | ASP |
| 12 | I | 24.12 | 24.05 | 10.02 | 9.08 | 12.31 | 51.59 | ILE |
| 13 | Q | 7.33 | 7.43 | 11.73 | 10.86 | 14.26 | 60.76 | GLN |
| 14 | K | 24.55 | 24.48 | 7.44 | 6.54 | 8.32 | 41.72 | LYS |
| 15 | V | 19.77 | 19.73 | 7.40 | 6.41 | 9.21 | 53.75 | VAL |
| 16 | A | 11.88 | 11.93 | 9.84 | 7.96 | 11.14 | 50.03 | ALA |
| 17 | G | 8.30 | 8.37 | 7.72 | 5.57 | 8.11 | 27.34 | GLY |
| 18 | T | 7.88 | 7.98 | 5.52 | 4.27 | 5.24 | 13.29 | THR |
| 19 | R | 13.77 | 13.98 | 2.37 | 0.68 | 0.56 | 1.37 | ARG |
| 20 | Y | 15.29 | 15.28 | 4.04 | 3.20 | | 60.67 | TYR |

SAMPLE: A-65 LACTOGLOBULINE

Sample Amount: 100 pmol

| AAcid # | AAcid ID | R.Time (min) | C.Time (min) | Pmol (raw) | Pmol (-bkgd) | Pmol (+lag) | Pmol Ratio | AAcid ID |
|---|---|---|---|---|---|---|---|---|
| 1 | L | 30.18 | 30.20 | 50.57 | 50.60 | 50.60 | 118.57 | LEU |
| 2 | I | 29.12 | 29.12 | 75.58 | 74.02 | 74.02 | 169.94 | ILE |
| 3 | V | 22.60 | 22.63 | 28.47 | 28.05 | 28.05 | 123.59 | VAL |
| 4 | T | 7.57 | 7.68 | 33.35 | 32.59 | 32.99 | 148.66 | THR |
| 5 | Q | 7.12 | 7.23 | 42.48 | 41.36 | 42.29 | 148.26 | GLN |
| 6 | T | 7.57 | 7.68 | 31.41 | 30.60 | 31.59 | 142.36 | THR |
| 7 | M | 22.13 | 22.17 | 21.52 | 21.18 | 21.53 | 109.34 | MET |
| 8 | K | 30.60 | 30.63 | 13.53 | 13.03 | 13.36 | 58.22 | LYS |
| 9 | G | 7.97 | 8.07 | 39.73 | 37.53 | 39.77 | 109.44 | GLY |
| 10 | L | 30.17 | 30.20 | 30.76 | 27.77 | 29.08 | 68.14 | LEU |
| 11 | D | 5.25 | 5.35 | 27.95 | 24.36 | 26.06 | 59.51 | ASP |
| 12 | I | 29.08 | 29.12 | 39.91 | 37.50 | 40.92 | 93.94 | ILE |
| 13 | Q | 7.13 | 7.23 | 30.21 | 28.35 | 30.90 | 108.31 | GLN |
| 14 | K | 30.58 | 30.63 | 9.32 | 8.66 | 9.35 | 40.77 | LYS |
| 15 | V | 22.58 | 22.63 | 13.70 | 12.67 | 13.43 | 59.18 | VAL |
| 16 | A | 11.97 | 12.07 | 21.03 | 17.50 | 19.65 | 71.54 | ALA |
| 17 | G | 7.98 | 8.07 | 19.46 | 16.79 | 19.13 | 52.65 | GLY |
| 18 | T | 7.57 | 7.68 | 7.37 | 6.43 | 7.51 | 33.86 | THR |
| 19 | W | 27.65 | 27.67 | 4.03 | 3.62 | 4.19 | 22.48 | TRP  |
| 20 | Y | 16.75 | 16.82 | 7.15 | 6.25 | | 41.54 | TYR |

METHOD FOR SEPARATING DIPHENYLUREA (DPU) AND PHENYLTHIOHYDANTOIN-TRYPTOPHAN (PTH-TRP) ALLOWING UNAMBIGUOUS IDENTIFICATION OF TRP IN AUTOMATIC SEQUENCE ANALYSIS

FIELD OF THE INVENTION

The present invention relates to a method of sequencing peptides which allows the unambiguous assignment of tryptophan residues by separating tryptophan residue derivatives from diphenylurea impurities during the sequencing process. In other aspects, the present invention relates generally to a method for chromatographic separation of tryptophan residue derivatives from diphenylurea.

BACKGROUND OF THE INVENTION

Gas-phase or pulsed liquid phase automated protein sequence analysis as originally described by Hunkapillar et al., Meth. Enzymol. 91: 399–413 (1983), has become the method of choice for determining primary structures of proteins, protein fragments and other peptides. This method has revolutionized the field of protein sequencing mainly because of the method's reliability, very high sensitivity, and wide applicability, as compared to previously used techniques. Gas phase protein sequencing, although an expensive analytical methodology, is now performed in a very large number of laboratories throughout the world and has become an essential and integral part of every biotechnology research effort. Instruments built according to the specifications of the Hunkapillar et al. method have become the industry-standard for protein sequencing, and are used in the vast majority of molecular biology laboratories. One such instrument manufactured by Applied Biosystems, Inc., Foster City, Calif., is described in U.S. Pat. Nos. 4,837,726 and 4,852,017.

Most protein/peptide sequencers use a chemical process modified from the Edman method for sequentially degrading peptides [Edman, Acta Chem. Scand. 4:283 (1950); Edman and Begg, Eur. J. Biochem. 1:80 (1967)]. The Edman method uses two repetitive chemical stages to, in effect, "clip off" amino acids one-by-one from one end of a peptide chain. In the first stage, phenyl isothiocyanate is coupled, in the presence of an organic base, to the amino-terminal amino acid of the peptide to be degraded. In the second stage, the coupled amino-terminal amino acid is "clipped off" or cleaved from the end of the peptide chain by treating the peptide with a strong organic acid. The cleaved amino acid residue derivative, an anilinothiazolinone (ATZ) derivative, is then collected as a sample for analysis. Successive repetition of these stages provides sequential samples which correspond to the amino acid sequence of the degraded peptide.

The collected samples are then analyzed to determine the amino acid content of the sample, thereby determining the peptide sequence. The ATZ derivative is usually converted to a more stable form, a phenylthiohydantoin (PTH) derivative, for analysis. In typical automated sequencers, such as the Applied Biosystems instrument and those described by Wittmann-Liebold et al., Anal. Biochem. 75:621 (1976) and Hewick et al., J. Biol. Chem. 256:7990 (1981), the PTH derivative is formed in a separate reaction vessel after the ATZ derivative has been collected from the peptide solution by extraction with an organic solvent. The extracted ATZ derivative is treated with an aqueous solution of a strong organic acid to produce the PTH derivative. The individual PTH derivative samples are then collected and saved for chromatographic analysis. In some automatic sequencers, the PTH derivatives are transferred directly to an analysis system which is part of the instrument [see for example the systems described by Machleidt and Hoffner in *Methods in Peptide and Protein Sequence Analysis*, Birr Ed. pp 35–47 (Elsevier 1980); and Wittman-Liebold and Ashman in *Modern Methods in Protein Chemistry*, Tschesche ed. pp. 303–27 (deGruyter 1985); Rodriguez, J. Chromatography 350:217 (1985)].

Usually the PTH derivatives are analyzed by high-performance liquid chromotography ("HPLC"). Reverse-phase HPLC ("RP-HPLC") using silica column packings has shown exceptional utility in peptide sequencing because (1) it is currently the only analytical method capable of reliably distinguishing between all PTH derivatives in a single analytical stage and (2) it is sufficiently sensitive to make sequencing of picomolar peptide samples possible.

However, current sequencing technology employing RP-HPLC is not without its problems. One significant drawback of present RP-HPLC methods, including those employed by the Applied Biosystems instrument and other conventional sequencing protocols, is that the presence of the PTH derivative of tryptophan ("PTH-Trp") cannot reliably be analyzed because RP-HPLC does not distinguish PTH-Trp from 1, 3-diphenylurea ("DPU"), a by-product of the sequential degradation process. This precludes unambiguous identification of tryptophan in sequencer cycles involving this amino acid, thus leading to potentially serious errors in protein sequence determination.

Thus there is a need to provide a method for reliable unambiguous determination of tryptophan residues in peptide sequences which employs a modified gradient protocol for reverse-phase HPLC of PTH amino acid derivatives. There is also a need to provide a method for separating DPU from PTH-Trp.

SUMMARY OF THE INVENTION

The present invention provides a reverse-phase HPLC method which allows the separation of DPU and PTH-Trp and, therefore, the correct assignment of tryptophan residues in an amino acid sequence. The method is based on a modification of the conventional HPLC gradient commonly used to elute and separate all PTH amino acids of interest in sequencing. In one embodiment, using automated instruments manufactured by Applied Biosystems, gradient modification is achieved by changing the manufacturer-supplied gradient program which controls the operation of the HPLC pumps in the instrument Using the methods of the present invention, the correct and reliable assignment of tryptophan residues is possible and reproducible over time, even with small sample sizes.

A method for sequencing a peptide is disclosed which comprises cyclicly degrading the peptide to form a plurality of amino acid residue samples., and subjecting such samples to reverse-phase high-performance liquid chromatography on a PTH-C18 column. The chromatography is performed using a two stage gradient of a first solution and a second solution. The first solution is an acetate buffer containing trimethylamine and tetrahydrofuran and having a pH of about 3.8 to about 4.6 depending on the optimal pH for a given column. The optimal pH for achieving the best separation for a given column can be determined in accordance with known methods. Preferably the first solution is made by mixing 22ml 3M sodium acetate pH 3.8, 6ml 3M sodium acetate pH 4.6, 500 ul 12.5% (v/v) trimethylamine and 1000ml 5% (v/v) tetrahydrofuran. In other embodiments the first solution components can be mixed in other proportions to achieve varying degrees of separation of PTH derivatives and impurities. Other such formulations were not observed to significantly affect separation of PTH-Trp from DPU. However, the specific formulation disclosed above was found to give the best separation of PTH derivatives and impurities, including PTH-Trp and DPU. The second solution comprises acetonitrile. Optionally, the second solution can contain dimethyl phenyl thiourea. In the disclosed embodiment, the second solution is acetonitrile containing 500 nmol/l dimethyl phenyl thiourea. Preferably the gradient is run at a flow rate of approximately 210 ul/minute.

The gradient has two stages: one stage of linearly varying concentration of the second solution and one stage of a constant concentration of the second solution. An exemplary gradient is depicted in FIG. 2. The depicted gradient begins with a first gradient stage during which the first solution and second solution are mixed to produce a substantially linear increase in the concentration of the second solution in the eluent from an initial concentration of about 7-13%, preferably about 11%, of the second solution by volume to a final concentration of about 32-36%, preferably about 34%, of the second solution by volume. The optimal mixture of solutions used at various stages of the gradients disclosed herein can differ from column to column. The optimal mixture for achieving the best separation on a given column can be determined in accordance with known methods. During the second gradient stage the concentration of the second solution in the eluent is maintained at a constant concentration of about 32-36%, preferably about 34%, of the second solution by volume.

In certain embodiments after the second gradient stage, when substantially all PTH amino acids have eluted from the column, the column may be washed. During the wash stage in one disclosed embodiment the first solution and second solution are mixed at a concentration of about 88-92%, preferably about 90%, of the second solution by volume. Any wash solution which will sufficiently wash the column may be employed.

In the disclosed embodiment the gradient is run at 210 ul/minute for a total of 33 minutes. In such embodiment, the first gradient stage runs for 25 minutes, the second gradient stage runs for an additional 5 minutes (i.e., until 30 minutes into the gradient), and the wash stage runs for an additional 3 minutes.

A method for separating 1,3-diphenylurea from phenylthiohydantoin-tryptophan in a sample is also disclosed comprising subjecting the sample to a reverse-phase high-performance liquid chromatography on a PTH-C18 column as described herein.

A method for determining the presence of tryptophan in a sample is also disclosed. Such method comprises treating the sample so as to form the phenylthiohydantoin derivative of amino acids present in the sample, and subjecting the treated sample to reverse-phase high-performance liquid chromatography on a PTH-C18 column as described herein.

In certain embodiments the gradient parameters (e.g., flow rate, solution mixture) can be controlled by computer. For example, in the disclosed embodiment, the gradient parameters are controlled by the processing unit of an automated sequencing instrument such as that manufactured by Applied Biosystems and described further below.

DESCRIPTION OF THE FIGURES

FIG. 6 is a summary of beta-lactoglobulin sequencing data from the first 20 cycles, indicating the amino acid sequence of the 20 N-terminal amino acids as determined using a standard HPLC protocol (FIG. 1). The erroneous assignment of arginine in cycle 19 (which should be Trp) is indicated by an arrow.

DETAILED DESCRIPTION

Sequence analysis was performed on an Applied Biosystems Model 477A protein sequencer equipped with an Applied Biosystems Model 120A on-line PTH amino acid analyzer. All operations using the Applied Biosystems instrument were carried out as prescribed in the manufacturer's user manual. A PTH-C18 reverse-phase column (Applied Biosystems part #0711-0203) was used for separation of PTH amino acid derivatives.

Chromatography solutions were as follows: Solution A was made by mixing 22 ml 3M sodium acetate pH 3.8 (Applied Biosystems #400319), 6 ml 3M sodium acetate pH 4.6 (Applied Biosystems #400199) with 500ul 12.5% (v/v) trimethylamine and 1000 ml 5% (v/v) tetrahydrofuran. Solution B consisted of acetonitrile containing 500 nmol/l of DMPTU (Applied Biosystems #400349). Unless otherwise stated, all solvents were analytical or spectroscopic grade. In disclosed embodiments, the column was equilibrated for 12.5 minutes with solution at a concentration of 11% Solution B by volume. Chromatography was performed at 50-55° C., preferably at 55° C.

Figure 1:
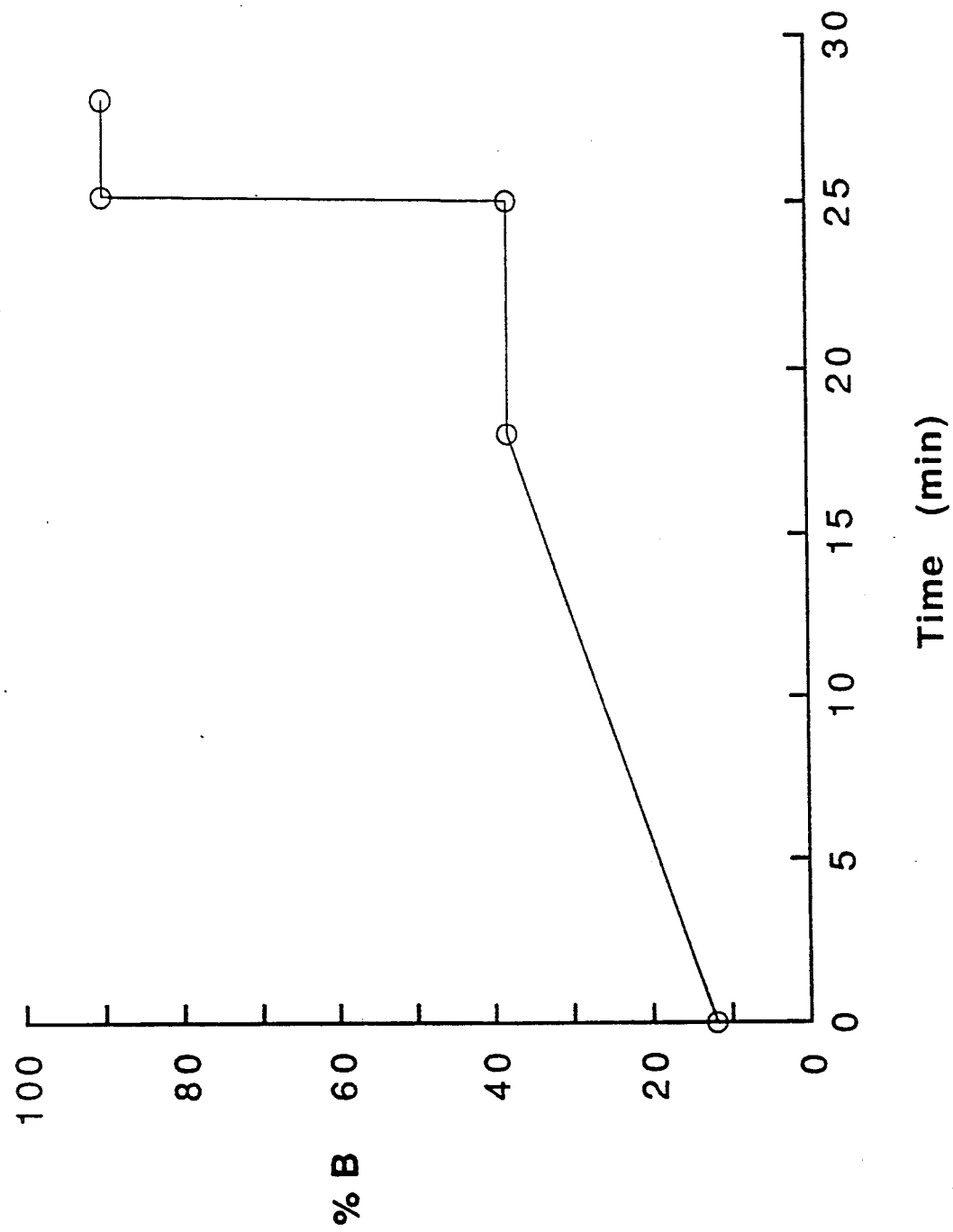
FIG. 1 is a graph depicting a standard gradient (12-38% Solution B in 18 min.; 7 min. isochratic at 38% Solution B; 3 min. wash at 90% Solution B) for separation of a mixture of PTH amino acid derivatives, as specified in the Applied Biosystems protein sequencer manual.
Figure 2:
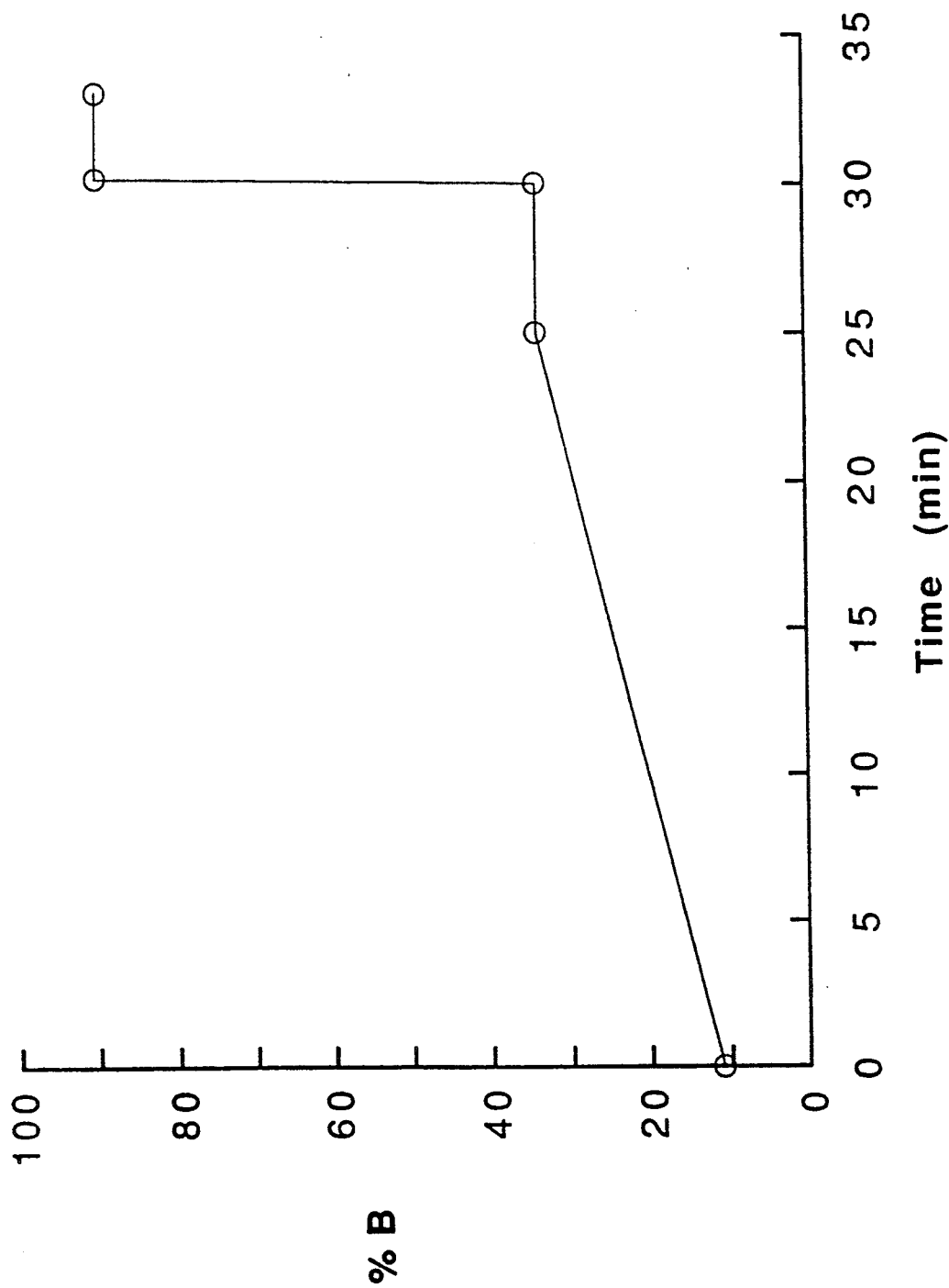
FIG. 2 is a graph depicting a gradient in accordance with the method of the present invention.

FIGS. 1 and 2 depict the gradients used to separate PTH amino acids. FIG. 1 depicts the standard protocol used with the Applied Biosystems analyzer. FIG. 2 depicts a preferred protocol of the present invention. When used, each set of gradient parameters was entered into the Applied Biosystems analyzer which then controlled the gradient.

In the protocol of the present invention shown in FIG. 2, the first gradient stage employs a substantially linear gradient starting at an initial concentration of 11% Solution B by volume in the elution solution and increasing to a final concentration of 34% Solution B by volume in 25 minutes. Although variations from 25 minutes for the first stage may produce separation, an exact time of 25 minutes has shown best separation. The second gradient stage employs a constant concentration of 34% Solution B by volume in the elution solution. After 30 minutes, the wash stage begins and employs 90% Solution B by volume in the elution solution.

Figure 3:
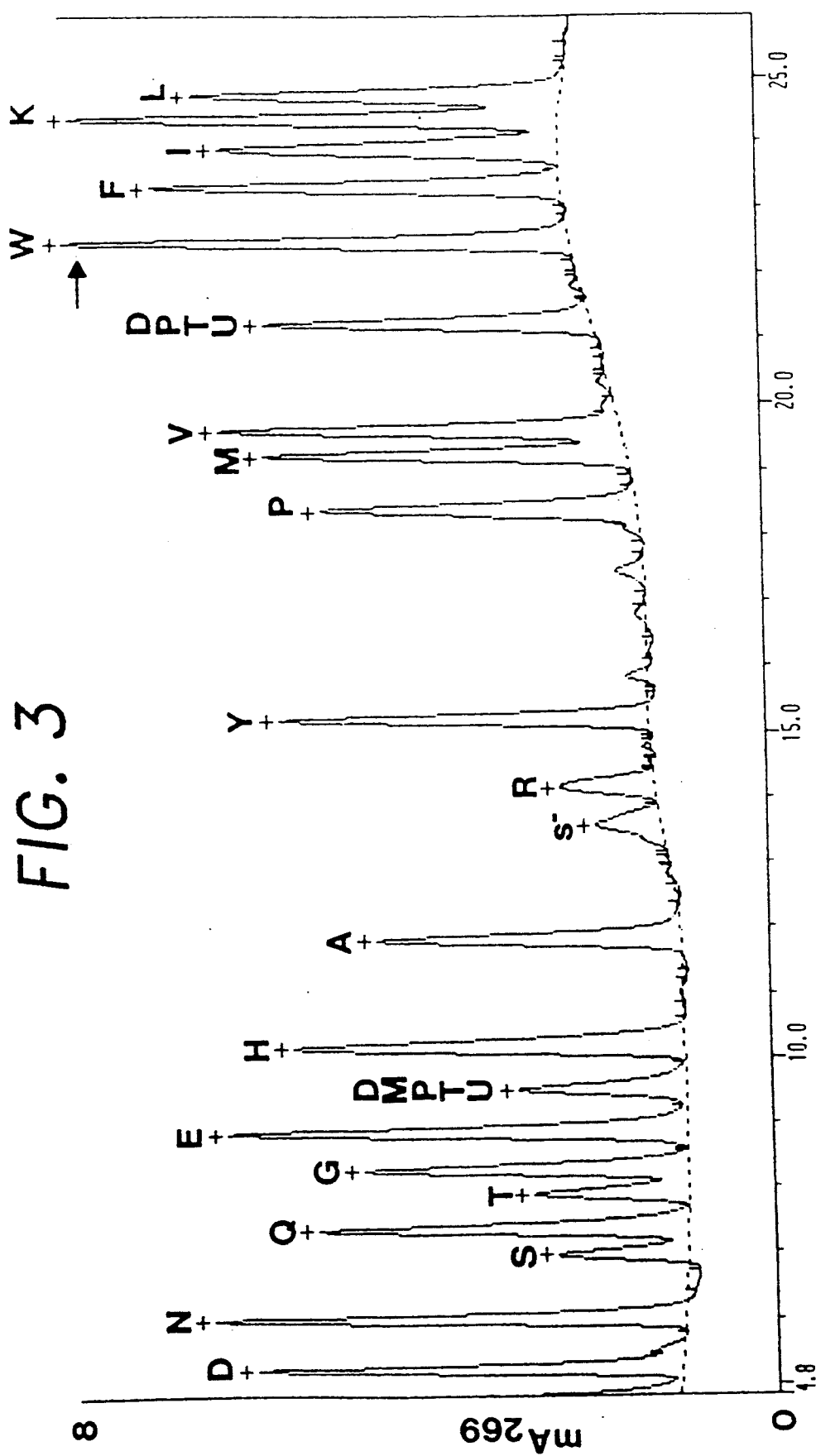
FIG. 3 is a chromatogram of a standard mixture of PTH amino acid derivatives (75 pmol of each PTH derivative) using standard gradient conditions (see FIG. 1). Peaks of PTH amino acid derivatives are identified by single letter codes for amino acids. "S−" denotes the dithiothreitol adduct of PTH-serine. DMPTU and DPTU are non-amino acid products generated by sequencer chemicals.

The standard gradient elution protocol shown in FIG. 1 and distributed commercially by Applied Biosystems for use with their automatic Model 470A and 477A Protein Sequencers and Model 120A PTH amino acid analyzers does not achieve separation of DPU and Trp. This is illustrated in FIG. 3 which depicts a chromatogram showing the separation of the standard PTH amino acids using the standard gradient protocol shown in FIG. 1. The PTH standard was acquired from Applied Biosystems. As indicated by the arrow, DPU and Trp elute as a single peak.

Figure 4:
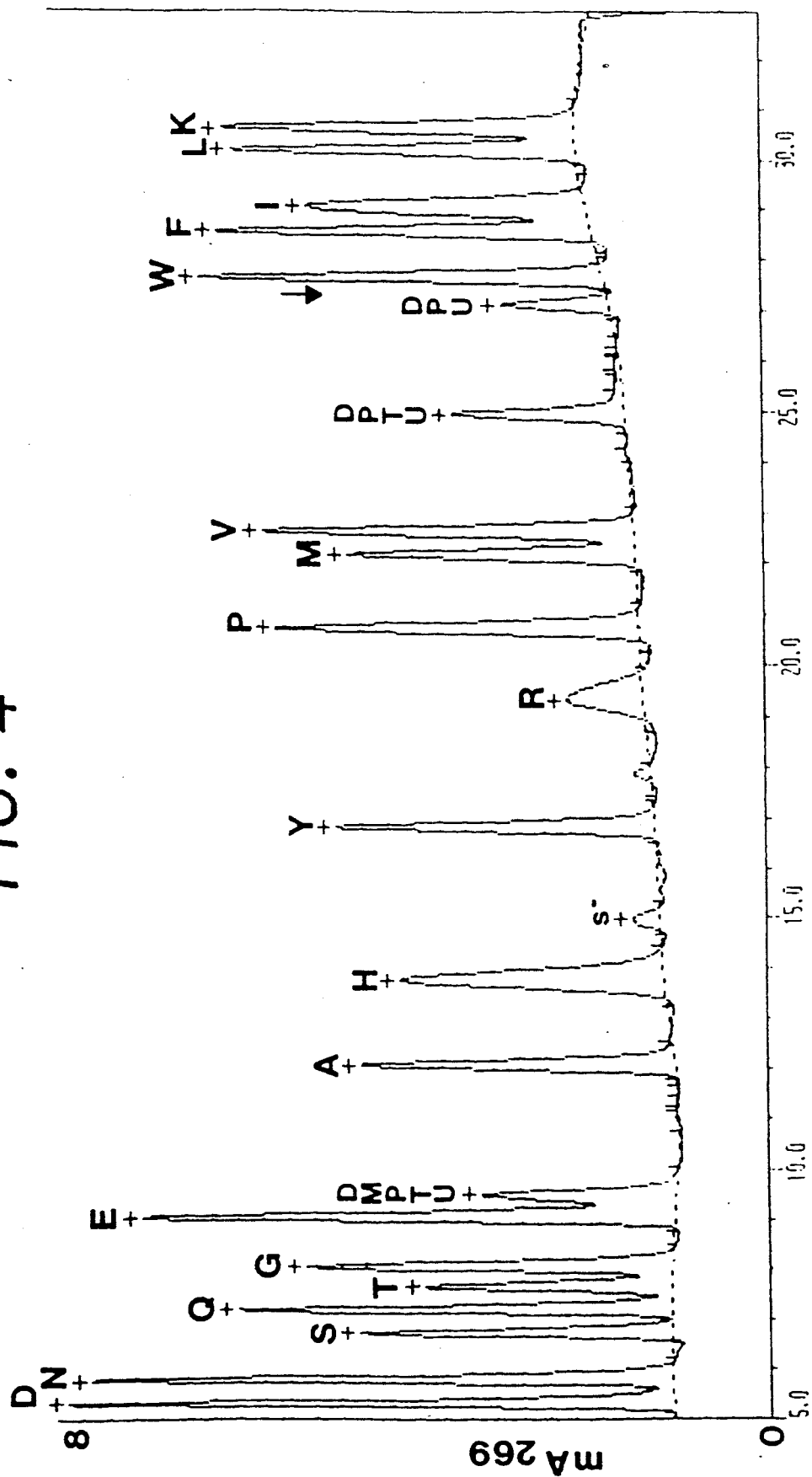
FIG. 4 is a chromatogram of a standard mixture of PTH amino acid derivatives (75 pmol of each PTH derivative) using a modified gradient protocol of the present invention (see FIG. 2). Peaks are denoted as in FIG. 3.

FIG. 4 is a chromatogram of the standard PTH amino acids after modification of the gradient protocol in accordance with the present invention as shown in FIG. 2. As indicated by the arrow, DPU and Trp are well separated under these conditions. All other PTH amino acids remain separated from each other and from method-generated substances giving rise to interfering chromatography peaks. All amino acids, including Trp can be identified, electronically integrated and quantitated with a high degree of accuracy.

It should be noted that the gradient modification causes the relative retention times of the PTH derivatives of lysine ("K") and leucine ("L") to change. While lysine elutes prior to leucine under standard conditions (FIG. 3), it elutes after leucine under modified conditions (FIG. 4). Furthermore, the peak of PTH-isoleucine broadens significantly when modified gradient conditions are used. However, these changes do not negatively impact on the reliability and accuracy of PTH amino acid identification and quantitation.

Figure 5:
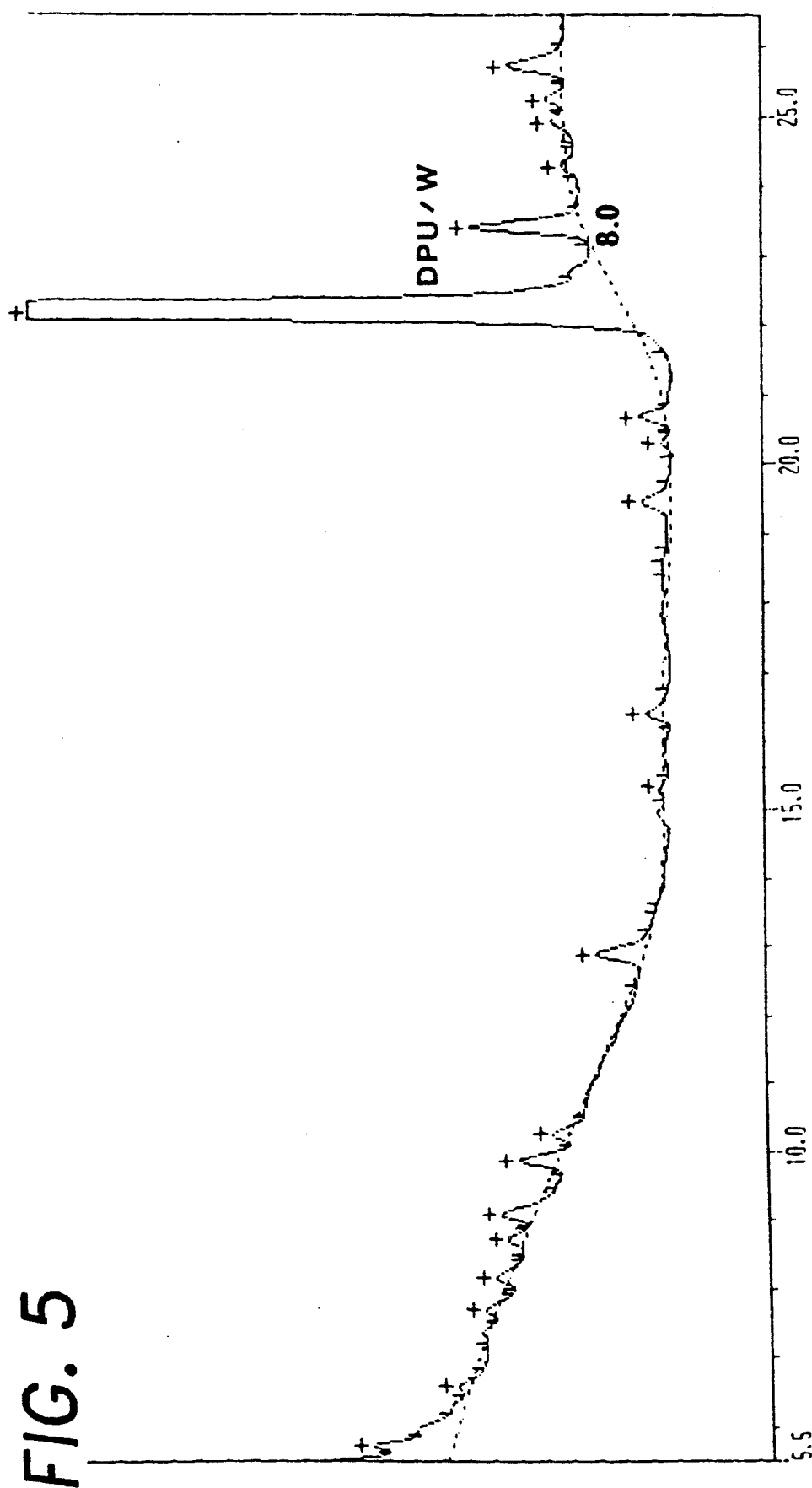
FIG. 5 is a chromatogram of the PTH amino acid derivative generated by cycle 19 of the sequence analysis of 100 pmol of beta-lactoglobulin and analyzed using a standard HPLC protocol (FIG. 1). The elution position of DPU and Trp is indicated. The number under the DPU/Trp peak indicates the calculated pmole amount for Trp, based on total peak area and the value for a Trp reference standard.

The quality and accuracy of sequencing results is also affected by the choice of HPLC gradient protocols. FIG. 5 depicts a chromatogram from cycle 19 of the sequence analysis of beta-lactoglobulin obtained with standard gradient conditions (FIG. 1). Beta-lactoglobulin was acquired from Applied Biosystems and is the standard used by Applied Biosystems for testing sequencer performance. It contains a Trp residue at position 19 from the N-terminus. In accordance with the data from FIG. 3, DPU and PTH-Trp coelute in the chromatogram shown in FIG. 5 which precludes the correct and unambiguous assignment of a PTH derivative in this cycle. In fact, the artificial intelligence routine which is used by the Applied Biosystems sequencer computer (for automatically assigning the sequence of a protein based on the chromatographic information obtained from the PTH analysis of all sequencer cycles) fails to identify Trp as the correct residue in cycle 19 and instead erroneously identifies the cycle as arginine ("Arg"). This is illustrated in FIG. 6 which shows the printout of the data for the first 20 amino acids of beta-lactoglobulin generated by the sequencer computer. Manual analysis of the data would also be ambiguous with respect to Trp identification in this cycle.

Figure 7:
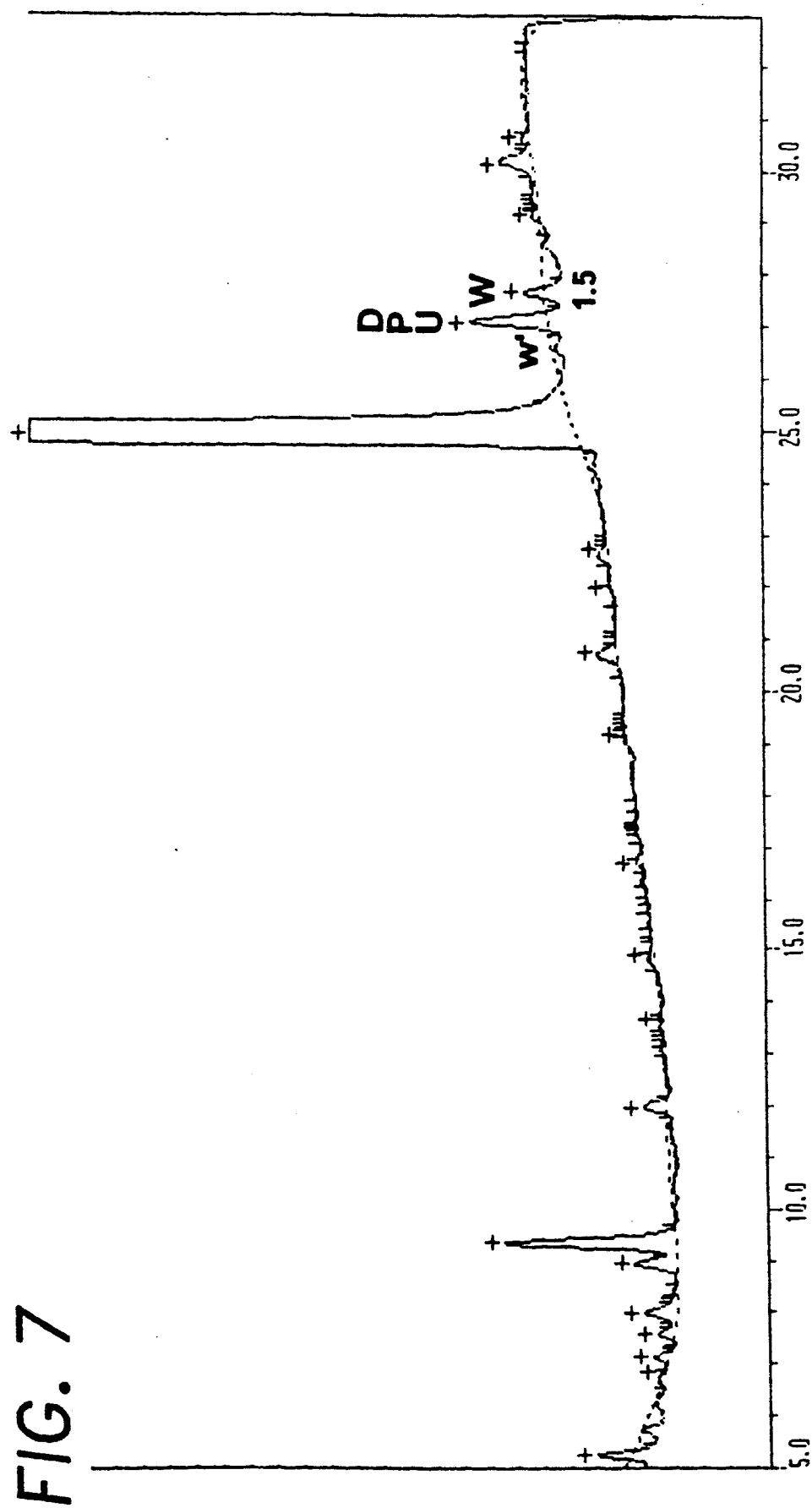
FIG. 7 is a chromatogram of the PTH derivatives generated by cycle 19 of the sequence analysis of 100 pmol of beta-lactoglobulin and analyzed using an HPLC protocol of the present invention (FIG. 2). Elution positions of PTH-Trp ("W"), a PTH-Trp derivative ("W'") and DPU are indicated. The number under the Trp peak indicates the amount in picomoles.
Figure 8:
FIG. 8 is a summary of beta-lactoglobulin sequencing data from the first 20 cycles, indicating the amino acid sequence of the 20 N-terminal amino acids, as determined using an HPLC protocol of the present invention (FIG. 2). The correct assignment of Trp at cycle 19 is indicated by an arrow.

In contrast, unambiguous identification of Trp in cycle 19 of a sequence analysis of beta-lactoglobulin is possible when a modified HPLC gradient protocol of the present invention (FIG. 2) is used. As shown in FIGS. 7 and 8, when samples are analyzed in accordance with the present invention, DPU and Trp elute separately and residue 19 is correctly identified as Trp by the sequencer computer.

Figure 9:
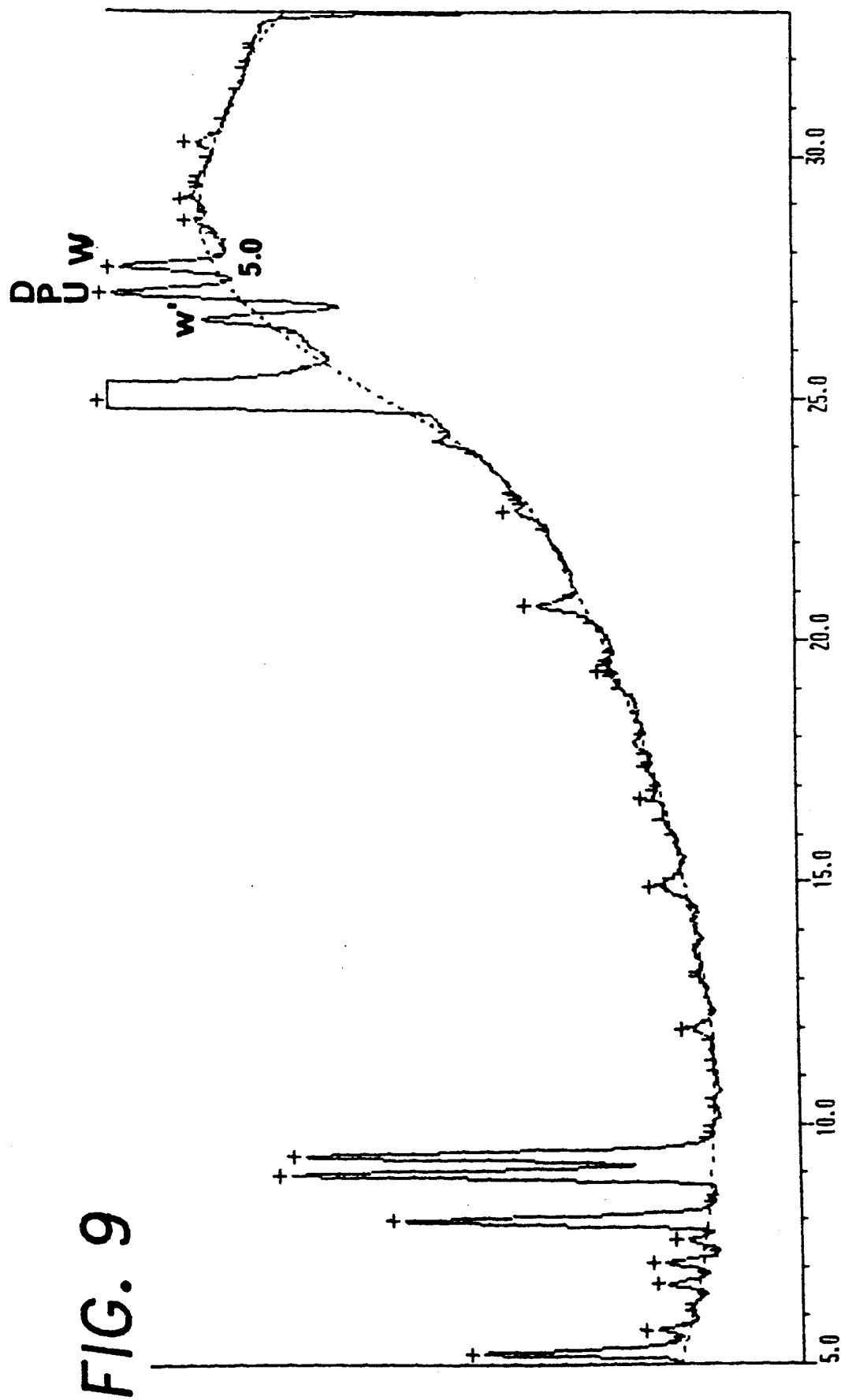
FIG. 9 is a chromatogram of PTH amino acid derivatives generated by cycle 11 of the sequence analysis of approximately 50 pmol of a *Staphylococcus aureus* V8 protease-generated fragment from a protein HBBM analyzed by an HPLC protocol of the present invention (FIG. 2). Elution positions of PTH-Trp ("W"), a PTH-Trp derivative ("W'") and DPU are indicated. The number under the Trp peak indicates the amount in picomoles.
Figure 10:
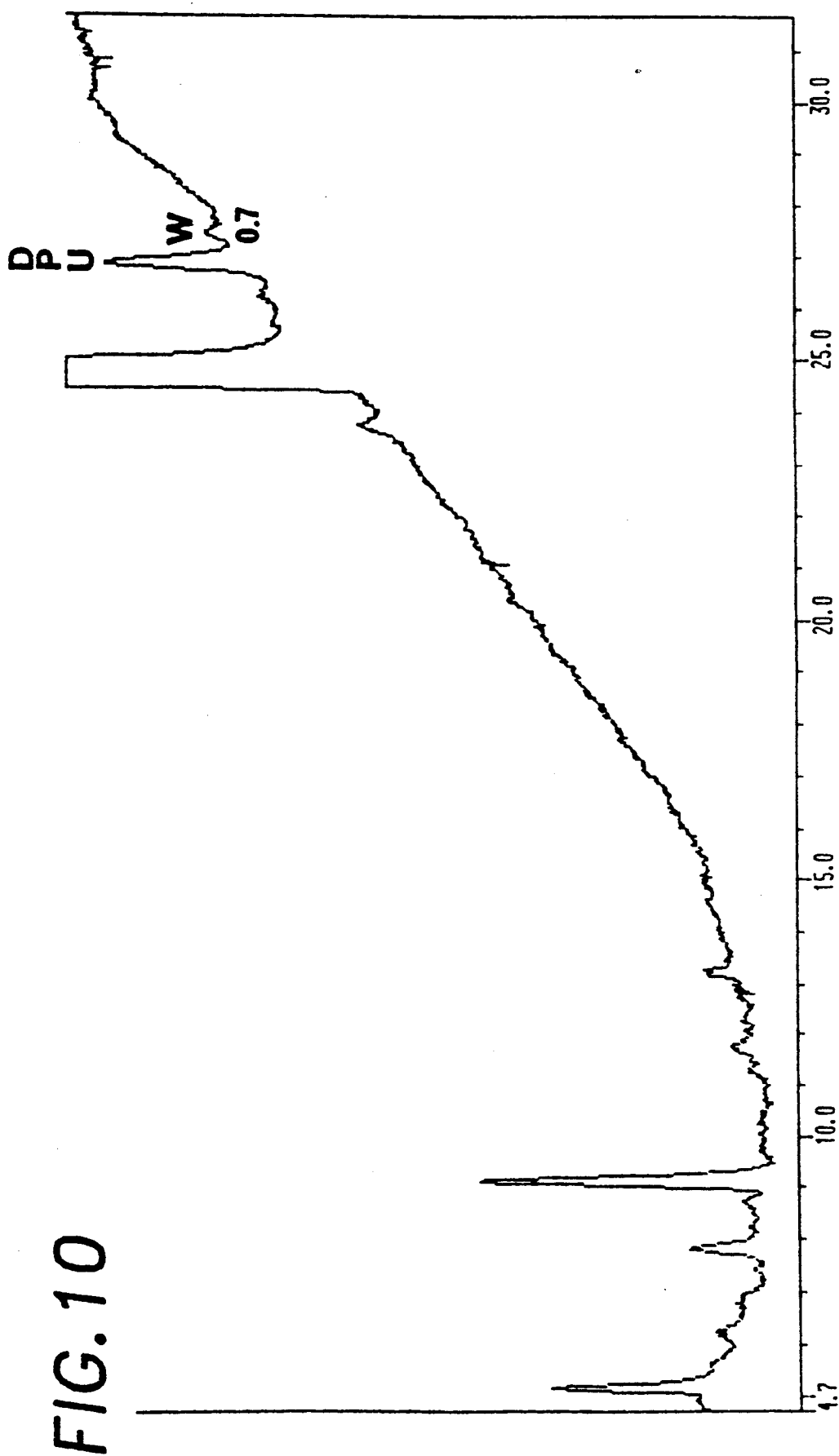
FIG. 10 is a chromatogram of PTH amino acid derivatives generated during cycle 5 of the sequence analysis of 5 pmol of a submaxillaris protease-generated fragment of the protein HBBM analyzed using an HPLC protocol of the present invention (FIG. 2). The peaks for PTH-Trp ("W") and DPU are indicated. The number under the Trp peak indicates the amount in picomoles.

The method of the present invention was also used to analyze PTH derivative samples from fragments of heparin binding brain mitogen ("HBBM"). FIG. 9 is a chromatogram generated from cycle 11 of the sequencing of approximately 50 pmol of a Staphylococous aureus V8 protease-generated fragment of HBBM. As indicated by the arrows, DPU and Trp eluted separately. Amino acid 11 of the fragment was correctly identified as Trp. FIG. 10 is a chromatogram generated from cycle 5 of the sequencing of 5 pmol of a submaxillaris protease-generated fragment of HBBM. As indicated by the arrows, again DPU and Trp eluted separately. Amino acid 5 of the fragment was again correctly identified as Trp. Even at this high sensitivity level with a very small peptide sample, the Trp assignment was still made due to the clear separation of DPU from the PTH-Trp derivative.

It should be noted that the generation of the PTH derivative of Trp is sometimes accompanied by the generation of an additional uncharacterized PTH derivative related to Trp (indicated by "W'"in FIGS. 7 and 9). This peak will allow the manual assignment of Trp even under conditions where PTH-Trp and DPU are not separated, but the generation of this peak is not predictable enough for unequivocal assignments of Trp under standard HPLC conditions (see for example FIGS. 7 and 8). With modified gradient conditions in accordance with the present invention, the peak W' is identified as an unknown peak and is not recognized by the peak assignment algorithm of the Applied Biosystems instrument. However, it does not interfere with the correct assignment of other PTH residues, including Trp, identified in chromatograms obtained with modified gradient conditions of the present invention.

The modified gradient conditions for PTH amino acids analysis proposed here are useful for analyzing Trp-containing protein and peptides. The correct assignment of Trp is achieved with a high degree of accuracy in conjunction with manual assignment procedures, but more importantly with automatic artificial intelligence methods, such as those presently used with Applied Biosystems, instrumentation and software. The procedure has been tested for a considerable number of polypeptides and was found to be reproducible. To this end, different batches of PTH-C18 columns were tested and found to provide reproducible separation of all PTH amino acids derivatives and to reliably separate DPU from PTH-Trp.

What is claimed is:

1. A method for determining the presence of tryptophan in a sample, said method comprising:

treating said sample so as to form the phenylthiohydantoin derivative of amino acids present in said sample; and subjecting said treated sample to reverse-phase high-performance liquid chromatography on a PTH-C18 reverse-phase column;

wherein said chromatography is performed using a two stage gradient of a first solution and a second solution;

wherein said first solution is an acetate buffer containing trimethylamine and tetrahydrofuran and having a pH of about 3.8 to about 4.6 and said second solution comprises acetonitrile;

wherein said gradient begins with a first stage during which said first solution and said second solution are mixed to produce a substantially linear increase in the concentration of said second solution from an initial concentration of about 7-13% of said second solution by volume to a final concentration of about 32-36% of said second solution by volume; and wherein a second stage follows said first stage wherein the concentration of said second solution is maintained at a constant concentration of about 32-36% of said second solution by volume.

2. The method of claim 1 wherein a wash stage follows said second stage.

* * * * *